United States Patent
Valentine et al.

(10) Patent No.: US 9,080,054 B2
(45) Date of Patent: Jul. 14, 2015

(54) MEDICAL DEVICE COMPRISING MACHINED PARTS AND INJECTION MOLDED PARTS

(75) Inventors: Craig Valentine, Thornton Cleveleys (GB); Vaughn Williams, Thornton Cleveleys (GB)

(73) Assignee: Invibio Limited, Lancashire (GB)

( * ) Notice: Subject to any disclaimer, the term of this patent is extended or adjusted under 35 U.S.C. 154(b) by 0 days.

(21) Appl. No.: 14/006,396

(22) PCT Filed: Mar. 21, 2012

(86) PCT No.: PCT/GB2012/050617
§ 371 (c)(1),
(2), (4) Date: Dec. 26, 2013

(87) PCT Pub. No.: WO2012/127228
PCT Pub. Date: Sep. 27, 2012

(65) Prior Publication Data
US 2014/0107299 A1   Apr. 17, 2014

(30) Foreign Application Priority Data
Mar. 22, 2011   (GB) .................................. 1104805.5

(51) Int. Cl.
C08L 71/12 (2006.01)
A61L 27/18 (2006.01)
A61L 31/06 (2006.01)
C08L 71/00 (2006.01)
B29C 45/00 (2006.01)

(52) U.S. Cl.
CPC ................. *C08L 71/12* (2013.01); *A61L 27/18* (2013.01); *A61L 31/06* (2013.01); *B29C 45/0001* (2013.01); *C08L 71/00* (2013.01); *C08G 2650/40* (2013.01); *Y10T 29/49* (2015.01)

(58) Field of Classification Search
CPC ..... A61L 27/18; A61L 31/06; B29C 45/0001; C08G 2650/40; C08L 71/00; C08L 71/12; Y10T 29/49
USPC .................... 525/390, 471; 264/297.2, 328.1, 264/328.14, 328.16
See application file for complete search history.

(56) References Cited

U.S. PATENT DOCUMENTS

2009/0326673 A1  12/2009  Devine et al.
2010/0305630 A1  12/2010  Warwick et al.

FOREIGN PATENT DOCUMENTS

WO   WO 2009/068915 A2  *  6/2009  ............. B29C 65/14

OTHER PUBLICATIONS

Gordon Jr., M.J.; Total Quality Process Control for Injection Molding, 2010, p. 394.*
Invibio, PEEK—Optima Polymer Processing Guide, 2004, p. 1-15.*

* cited by examiner

*Primary Examiner* — Robert Jones, Jr.
(74) *Attorney, Agent, or Firm* — Hodgson Russ LLP

(57) ABSTRACT

A medical device comprises parts made by injection moulding and parts made by machining such that the respective parts have similar colors, measured on the L*, a*, b* scale. The parts made by injection moulding may be made in a process which involves introducing molten material comprising polymeric material such as PEEK into a mould, wherein a mould surface which contacts the molten material is at a temperature of at least 210° C. and maintaining the molten material in the mould for at least 90 seconds.

21 Claims, No Drawings

MEDICAL DEVICE COMPRISING MACHINED PARTS AND INJECTION MOLDED PARTS

This invention relates to a medical device and particularly, although not exclusively, relates to a medical device made from a plurality of components.

Polyetheretherketone (PEEK) polymer is widely used in making bio-compatible implants such as devices for spinal applications due to its excellent properties, such as of bio-compatibility, strength, flexibility and wear resistance.

Many medical devices are made by machining from solid PEEK rod or other stock shapes. However, machining is time-consuming and there can be a significant amount of wasted material. As a result, it is desirable to produce medical devices or parts thereof by injection moulding which tends to be cheaper, quicker and less wasteful of materials. Injection moulding of PEEK-Optima polymer (a PEEK polymer obtainable from Invibio Limited) may be undertaken as described in a PEEK-Optima processing guide available from www.invibio.com. The guide advocates use of a standard reciprocating screw injection moulding machine which is able to reach 400° C. It is recommend to inject into a mould having a surface temperature in the range 175 to 205° C. to achieve good mould filling and crystallinity.

It is not always convenient or cost effective to immediately change production of a medical device which comprises a multiplicity of parts from all the parts being machined to all the parts being injection moulded. Thus, in moving over to production of all parts of a medical device by injection moulding, it is desirable to be able to go through a transitional phase wherein some parts of a device are made by injection moulding and some are made by machining. Then, over a period of time, more and more parts of a device may be produced by injection moulding until all parts of the device are made by injection moulding. The transition phase may however extend over several years.

There is a problem in providing a medical device which is made up of a multiplicity of PEEK (or other) polymer parts, some of which are made by machining and some of which are made by injection moulding in that machined parts tend to be a significantly lighter colour compared to parts made by injection moulding.

It is generally aesthetically unacceptable to provide a medical device and/or a kit of parts for a medical device which includes PEEK polymer parts of significantly different colours and/or shades; the different colours/shades may be perceived by surgeons and/or patients as indicating defective parts and/or parts of variable and/or low quality. Such a perception is clearly undesirable.

It is an object of the present invention to address the above described problems.

According to a first aspect of the invention, there is provided a plurality of components for a medical device, or being part of the whole of an assembled medical device, said plurality of components including:

(i) a first component made in a process which comprises machining;

(ii) a second component made in a process which comprises moulding, for example injection moulding; wherein (iii) said first component comprises a polymeric material which comprises a repeat unit of formula

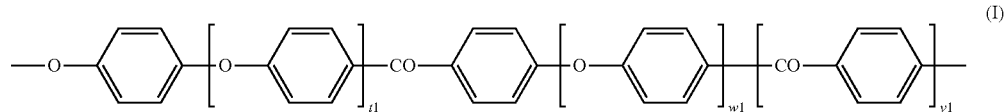

(iv) said second component comprises a polymeric material which comprises a repeat unit of formula

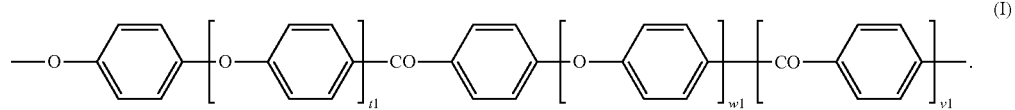

In the following, colour is expressed in accordance with the CIE 1976 (L*, a*, b*) colour space. It may be measured using a Minolta CR410 Chromameter Colour values described herein are suitably determined on a substantially flat part of a component being tested. Values are suitable assessed at a single position on a component. An average value relating to values of the single position may be determined.

The L* at a first position on the first component may have a value "X" and the L* at a first position on the second component may have a value "Y". The L* difference, defined as X minus Y, may be less than 8, suitably less than 7.5, preferably less than 7.0, more preferably less than 6.6. The L* difference may be more than 3, 4 or 5.

The ratio of X:Y may be less than 1.15, preferably less than 1.13, more preferably less than 1.12. The ratio may be greater than 1 or 1.05.

The a* at said first position on the first component may have a value "E" and the a* at said first position on the second component may have a value "F". The a* difference, defined as F minus E, may be less than 0.5, suitably less than 0.4, preferably less than 0.35. The a* difference may be more than 0.2 or 0.25.

The ratio F:E may be less than 1.4 or less than 1.3. It may be greater than 1 or 1.1.

The b* at said first position on the first component may have a value "P" and the b* at said first position on said second component may have a value Q. The b* difference, defined as Q minus P, may be less than 3, suitably less than 2, preferably less than 1. It may be at least 0.3 or 0.5.

The ratio of Q:P may be less than 0.3 or less than 0.15. It may be greater than 1.

Unless otherwise stated, in the context of the present specification, a "major amount" may mean at least 60%, at least 70%, at least 80%, at least 90%, at least 95% or, especially, at least 99%.

Said second component may have an L* of greater than 60, preferably greater than 61, more preferably greater than 62. The L* may be less than 69 or 68.

Said second component may have an a* of less than 1.8, preferably less than 1.6. The a* may be greater than 1 or 1.2.

Said second component may have a b* of less than 15, preferably less than 13. The b* may be greater than 11 or 11.5.

Preferably, a major percentage of the surface area of the second component is defined by the shape of a mould used in injection moulding the second component. Less than 10%, or less than 5% of the surface area of the second component may be defined by a means other than the shape of a mould. Preferably, in a preferred embodiment, substantially the only areas of said second component which may not be directly defined by the shape of the mould are: one or a plurality of parts of the second component which were connected to a vestige or sprue as part of the injection moulding process; and/or areas in which openings are defined in the second component for example by drilling or the like.

In one embodiment, the second component may be made from a near net-shaped component by treatment, for example selective machining, of the near net-shaped component. The near net-shaped component may be produced by moulding, for example injection moulding. In the component, an area, for example a major area, of the near net-shape may not be machined in defining the second component.

A skilled person in the art will be able, by routine visual and/or analytical techniques to determine whether a component has been produced by moulding, for example injection moulding or by machining. For example, the surface of the component may be flatter and/or smoother than attainable by other techniques such as machining.

Preferably, a major percentage of the surface area of the first component is defined by machining. Preferably, substantially the entirety of the surface area is defined by machining.

Said first component is suitably not subjected to any injection moulding step during any part of its production or during production of any precursor used in the production of said first component.

A skilled person in the art will be able, by routine visual and/or analytical techniques to determine whether a component has been made by machining. For example, machining (e.g. milling) marks may be visible under the naked eye; and, in general, microscopic analysis will show moulded surfaces to be flatter compared to machined surfaces.

A machined part produced from an extruded blank may include an internal region, for example a core region, which is darker or lighter than regions around the internal region. This may be due to different levels of crystallinity of the internal region compared to regions around the internal region.

Said polymeric material may be amorphous or semi-crystalline. Said polymeric material is preferably semi-crystalline. The level and extent of crystallinity in a polymer is preferably measured by wide angle X-ray diffraction (also referred to as Wide Angle X-ray Scattering or WAXS), for example as described by Blundell and Osborn (Polymer 24, 953, 1983). Alternatively, crystallinity may be assessed by Differential Scanning calorimetry (DSC).

The level of crystallinity in said polymeric material may be at least 1%, suitably at least 3%, preferably at least 5% and more preferably at least 10%. In especially preferred embodiments, the crystallinity may be greater than 30%, more preferably greater than 40%, especially greater than 45%.

The main peak of the melting endotherm (Tm) for said polymeric material (if crystalline) may be at least 300° C.

Preferred polymeric materials have a said repeat unit wherein $t1=1$, $v1=0$ and $w1=0$; $t1=0$, $v1=0$ and $w1=0$; $t1=0$, $w1=1$, $v1=2$; or $t1=0$, $v1=1$ and $w1=0$. More preferred have $t1=1$, $v1=0$ and $w1=0$; or $t1=0$, $v1=0$ and $w1=0$. The most preferred has $t1=1$, $v1=0$ and $w1=0$.

In preferred embodiments, said polymeric material is selected from polyetheretherketone, polyetherketone, polyetherketoneetherketoneketone and polyetherketoneketone. In a more preferred embodiment, said polymeric material is selected from polyetherketone and polyetheretherketone. In an especially preferred embodiment, said polymeric material is polyetheretherketone.

Said polymeric material suitably has a melt viscosity (MV) of at least $0.06$ $kNsm^{-2}$, preferably has a MV of at least $0.085$ $kNsm^{-2}$, more preferably at least $0.12$ $kNsm^{-2}$, especially at least $0.14$ $kNsm^{-2}$.

MV is suitably measured using capillary rheometry operating at 400° C. at a shear rate of $1000$ $s^{-1}$ using a tungsten carbide die, 0.5×3.175 mm.

Said polymeric material may have a MV of less than 1.00 $kNsm^{-2}$, preferably less than 0.5 $kNsm^{-2}$.

Said polymeric material may have a MV in the range 0.09 to 0.5 $kNsm^{-2}$, preferably in the range 0.14 to 0.5 $kNsm^{-2}$.

Said polymeric material may have a tensile strength, measured in accordance with ISO527 (specimen type 1b) tested at 23° C. at a rate of 50 mm/minute of at least 20 MPa, preferably at least 60 MPa, more preferably at least 80 MPa. The tensile strength is preferably in the range 80-110 MPa, more preferably in the range 80-100 MPa.

Said polymeric material may have a flexural strength, measured in accordance with ISO178 (80 mm×10 mm×4 mm specimen, tested in three-point-bend at 23° C. at a rate of 2 mm/minute) of at least 50 MPa, preferably at least 100 MPa, more preferably at least 145 MPa. The flexural strength is preferably in the range 145-180 MPa, more preferably in the range 145-164 MPa.

Said polymeric material may have a flexural modulus, measured in accordance with ISO178 (80 mm×10 mm×4 mm specimen, tested in three-point-bend at 23° C. at a rate of 2 mm/minute) of at least 1 GPa, suitably at least 2 GPa, preferably at least 3 GPa, more preferably at least 3.5 GPa. The flexural modulus is preferably in the range 3.5-4.5 GPa, more preferably in the range 3.5-4.1 GPa.

Said first component suitably includes at least 80 wt %, preferably at least 90 wt %, more preferably at least 95 wt %, especially at least 99 wt % of a said polymeric material Said first component preferably includes only one type of polymeric material of formula I, preferably polyetheretherketone.

Said second component suitably includes at least 80 wt %, preferably at least 90 wt %, more preferably at least 95 wt %, especially at least 99 wt % of a said polymeric material. Said second component preferably includes only one type of polymeric material of formula I, preferably polyetheretherketone.

Said first and second components preferably comprise the same type of polymeric material of formula I. The MV of the polymeric material of the first and second components may be substantially the same. Preferably, said first and second components have substantially the same composition.

Said medical device may be for implantation in a human body. It may be an orthopaedic device, for example a spinal device. It may be an orthopaedic device for use in spinal fusion, spinal non-fusion, arthroscopy/sports medicine, trauma and artificial joint replacement. It may comprise a spinal cage or spinal rod. It may comprise a suture anchor or interference screw.

Suitably, said plurality of components is for a medical device. Said components may be provided in a kit, for example in a receptacle.

Said plurality of components may include at least two components made in a process which comprises machining. Said at least two components may independently have any features of a said first component described herein.

Said plurality of components may include at least two components made in a process which comprises injection moulding, wherein suitably said at least two components may independently have any features of said second component described herein. The number of second components in said plurality of components made in a process which comprises injection moulding may be greater than the number of first components in said plurality of components made in a process which comprises machining.

The invention extends to an assembled medical device including a plurality, suitably three or more, components as described herein, wherein said components include a said first component and a said second component as described.

According to a second aspect of the invention, there is provided a second component as described according to the first aspect per se.

According to a third aspect of the invention, there is provided a method of making a second component for said plurality of components of the first aspect, said method comprising:

(i) introducing molten material comprising polymeric material of formula I as described according to the first aspect into a mould, wherein a mould surface which contacts the molten material is at a temperature of at least 210° C.; and (ii) maintaining said molten material in said mould for at least 90 seconds.

Said polymeric material introduced in step (i) may have any feature of the polymeric material of the first aspect. It preferably is of formula I wherein v1=0 and w1=0. Preferably, it comprises polyetheretherketone.

Said second component made in the method may have any feature of the second component of the first aspect. The molten material is therefore suitably selected to make a second component having the composition specified according to the first aspect when material is ejected from the mould.

Said molten material introduced in step (i) may include at least 90 wt %, preferably at least 95 wt %, more preferably at least 99 wt % of a said polymeric material (preferably a single type of polymeric material) of formula I.

Said molten material may be at a temperature of at least 340° C., suitably at least 350° C., preferably at least 360° C., more preferably at least 370° C. immediately prior to introduction into said mould. It may be at a temperature of less than 410° C., preferably less than 400° C.

The temperature of a mould surface which contacts the molten material immediately prior to contact with said molten material may be at least 210° C. Said temperature may be at least 220° C., suitably at least 230° C., preferably at least 240° C. immediately prior as aforesaid. The temperature immediately prior to contact may be less than 270° C., preferably less than 265° C., more preferably 260° C. or less. Preferably, the temperature immediately prior is in the range 235° C. to 260° C., more preferably 240° C. to 260° C.

Said mould surface may be at a temperature of at least 210° C., suitably at least 220° C., preferably at least 230° C., more preferably at least 240° C. for substantially the entire time for which the molten material (e.g. the polymeric material of formula I) is in contact with it.

Said molten material may be maintained in the mould for at least 120 seconds, preferably at least 150 seconds, more preferably at least 170 seconds, especially at least 180 seconds. The total time elapsing from initial contact of molten material with the mould surface and ejection of a said component from the mould may be less than 600 seconds, suitably less than 500 seconds, preferably less than 400 seconds, more preferably less than 300 seconds, especially less than 250 seconds. Suitably, the molten material solidifies as it cools during its time in the mould.

In a preferred embodiment, the temperature of said mould surface immediately prior to contact with said molten material is in the rage 230° C. to 260° C. (preferably 240° C. to 260° C.) and the total time elapsing from initial contact of molten material with the mould surface and ejection of said component from the mould is in the range 150 to 500 seconds (preferably 170 to 300 seconds) and the mould surface is at a temperature of at least 230° C. for substantially the entire time said molten material is in the mould.

On ejection of material from the mould, the material is suitably subjected to ambient temperature, typically in the range 15° C. to 30° C. It is suitably not reheated at any time to a temperature which is greater than 200° C., or greater than 150° C., or greater than 110° C.

In step (i), the molten material is suitably injected into the mould preferably using an injection pressure in the range 5 to 15 MPa, for example 7 to 14 MPa.

Preferably, the mould is maintained under ambient atmospheric conditions whilst the molten material is present therein; that is, the mould and/or the molten material introduced thereinto, is suitably not under an atmosphere which is concentrated in an inert gas, such as nitrogen.

Said second component is preferably not subjected to an annealing step after ejection from said mould.

According to a fourth aspect of the invention, there is provided a method of making a plurality of components for a medical device according to the first aspect, the method comprising:

(i) making a second component as described according to the third aspect;

(ii) making a first component by machining a blank which comprises a polymeric material of formula I.

The method may include incorporating the plurality of components in a kit for example comprising a receptacle in which the plurality of components is arranged.

According to a fifth aspect of the invention, there is provided a method of assembling a medical device, for example a device for implantation in the human body, the method comprising:

(i) selecting a first component for a medical device as described herein;

(ii) selecting a second component for the medical device as described herein;

(iii) optionally, selecting additional components for the medical device;

(iv) juxtaposing, preferably contacting, more preferably connecting, the first and second components and optional additional components thereby to define the medical device.

Any invention described herein may be combined with any feature of any aspect of any other invention or embodiment described herein mutatis mutandis.

Specific embodiments of the invention will now be described, by way of example.

The following material is referred to hereinafter.

PEEK OPTIMA LT1—polyetheretherketone (PEEK) polymer obtained from Invibio Limited, UK.

Spinal rods, such as described in for example US2009/0248080, WO2008/027860 and U.S. Pat. No. 6,596,992 may comprise a plurality of parts. It may be desirable in some situations, for example to address the problems described in the introduction of the present specification, to produce some parts of a device by injection moulding and some parts of the device by machining.

The following examples illustrate how parts may be made having different colours, measured as L*, and how process conditions may be adjusted to provide injection moulded parts which are a relatively close and aesthetically-acceptable colour match to machined parts, thereby enabling such injection moulded and machined parts to be included in a kit of parts of a medical device and/or in an assembled medical device.

EXAMPLE 1

PEEK OPTIMA LT1 rod was produced by extrusion under appropriate conditions (360° C. to 400° C.). After cooling, it was machined to define a machined rod.

EXAMPLE 2

An injection moulding machine was purged with PEEK-OPTIMA LT1 which had been dried for more than 12 hours at 120° C. Further PEEK-OPTIMA LT1 was then injection moulded into test bars. The mould temperature (i.e. the actual tool face temperature rather than the set point temperature of the mould) was 180° C. and the test bars were retained in the mould for 180 seconds before being ejected. As will be appreciated, the mould is cooler than the molten PEEK which contacts it and will therefore solidify the PEEK. The temperature of the mould was not allowed to fall below 180° C. whilst the PEEK was present therein.

EXAMPLES 3 AND 4

The procedure of Example 2 was following to produce further test bars, except that the mould temperatures were 220° C. and 240° C. respectively.

EXAMPLE 5

Assessment of Colour of Test Pieces

A Minolta CR410 Chromameter was used to assess the LAB values of the test bars of Examples 1 to 4. Results are provided below.

| Example No. | Summary of process | L* | a* | b* |
|---|---|---|---|---|
| 1 | Machined | 69.19 | 1.17 | 11.31 |
| 2 | Mould surface 180° C.; ejection after 3 mins | 58.95 | 2.05 | 17.05 |
| 3 | Mould surface 220° C.; ejection after 3 mins | 61.70 | 1.47 | 13.75 |
| 4 | Mould surface 240° C.; ejection after 3 mins | 62.78 | 1.51 | 12.00 |

OTHER EXAMPLES

In other examples, it was noted that for shorter retention times in the mould (e.g. less than 180 seconds) the L values of the moulded test pieces were darker than when retention times were 180 seconds. Furthermore, for mould temperatures greater than 260° C., the L values were lower, indicating lower lightness and/or increased darkness.

DISCUSSION

It is clear from the examples that the lightness (L) of injection moulded samples is increased for mould temperatures of 220° C. or 240° C. and a retention time of 3 minutes compared to lower mould temperatures and/or retention times. The colour achieved makes injection moulded samples closer in colour to those made by machining. As a result, parts for a respective medical device may be made by both machining and injection moulding with the resulting kit of parts and/or device having a more aesthetically acceptable overall colour.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A plurality of components for a medical device, or being part of the whole of an assembled medical device, said plurality of components including:
   (i) a first component made in a process which comprises machining;
   (ii) a second component made in a process which comprises moulding; wherein
   (iii) said first component comprises a polymeric material which comprises a repeat unit of formula

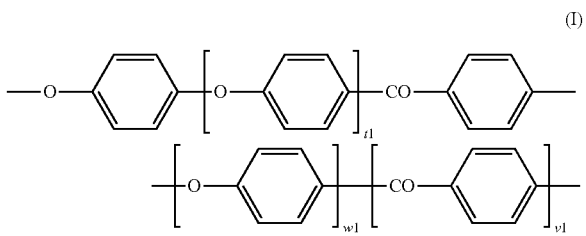

(iv) said second component comprises a polymeric material which comprises a repeat unit of formula

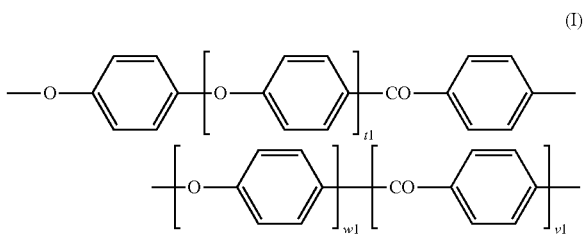

wherein t1, w1, v1 independently represent 0, 1 or 2, and the L* at a first position on the first component has a value "X" and the L* at a first position on the second component has a value "Y", wherein the L* difference, defined as X minus Y, is less than 8.

2. A plurality of components according to claim 1, wherein the a* at said first position on the first component has a value "E" and the a* at said first position on the second component has a value "F", wherein the a* difference, defined as F minus E, is less than 0.5; and the b* at said first position on the first component has a value "P" and the b* at said first position on said second component has a value "Q", wherein the b* difference, defined as Q minus P, is less than 3.

3. A plurality of components according to claim 1, wherein said second component has an L* of greater than 60, an a* of less than 1.8 and a b* of less than 15.

4. A plurality of components according to claim 1, wherein said first and second components comprise the same type of polymeric material of formula I.

5. A plurality of components according to claim 1, wherein said first and second components have substantially the same composition.

6. A plurality of components according to claim 1, wherein said first and second components comprise polyetheretherketone.

7. A plurality of components according to claim 1, including at least two components made in a process which comprises machining; and/or at least two components made in a process which comprises injection moulding.

8. A plurality of components according to claim 1, being part of an assembled medical device.

9. A method of making a second component for said plurality of components of claim 1, said method comprising:
(i) introducing molten material comprising polymeric material of formula

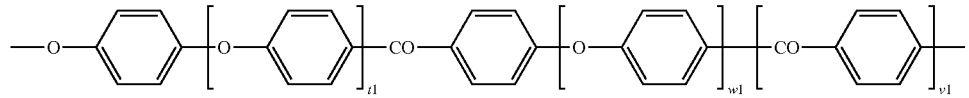

wherein t1, w1, v1 independently represent 0, 1 or 2 into a mould, wherein a mould surface which contacts the molten material is at a temperature of at least 210° C.; and
(ii) maintaining said molten material in said mould for at least 90 seconds.

10. A method according to claim 9, wherein said molten material is at a temperature of at least 340° C. immediately prior to introduction into said mould.

11. A method according to claim 9, wherein said molten material is at a temperature of at least 370° C. immediately prior to introduction into said mould.

12. A method according to claim 9, wherein the temperature of a mould surface which contacts the molten material is at a temperature of at least 210° C. immediately prior to contact with said molten material.

13. A method according to claim 12, wherein said mould surface is at a temperature of at least 240° C.

14. A method according to claim 9, wherein said molten material is maintained in the mould for at least 120 seconds.

15. A method according to claim 9, wherein the total time elapsing from initial contact of molten material with the mould surface and ejection of a said component from the mould is less than 600 seconds.

16. A method according to claim 9, wherein the temperature of said mould surface immediately prior to contact with said molten material is in the range 230° C. to 260° C. and the total time elapsing from initial contact of molten material with the mould surface and ejection of said component from the mould is in the range 150 to 500 seconds and the mould surface is at a temperature of at least 230° C. for substantially the entire time said molten material is in the mould.

17. A method according to claim 9, wherein the mould is maintained under ambient atmospheric conditions whilst the molten material is present therein.

18. A method according to claim 9, wherein said second component is not subjected to an annealing step after ejection from said mould.

19. A method of making a plurality of components for a medical device, the method comprising:
(i) making a second component as described in claim 9;
(ii) making a first component by machining a blank which comprises a polymeric material of formula:

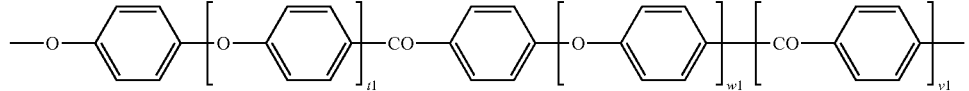

wherein t1, w1, v1 independently represent 0, 1 or 2.

20. A method according to claim 19, which includes incorporating the plurality of components in a kit comprising a receptacle in which the plurality of components is arranged.

21. A plurality of components according to claim 1, wherein the L* difference is less than 7.0.

* * * * *